US00PP34974P3

(12) United States Plant Patent

Scalzo et al.

(10) Patent No.: US PP34,974 P3
(45) Date of Patent: Feb. 14, 2023

(54) BLUBERRY PLANT NAMED 'C13-051'

(50) Latin Name: ***Vaccinium corymbosum* hybrid**
Varietal Denomination: C13-051

(71) Applicants: Costa Berry International Pty Ltd, Ravenhall (AU); Florida Foundation Seed Producers, Inc., Marianna, FL (US)

(72) Inventors: Jessica Scalzo, Corindi Beach (AU); Paul M. Lyrene, Micanopy, FL (US)

(73) Assignees: COSTA BERRY INTERNATIONAL PTY LTD, Revenhall (AU); FLORIDA FOUNDATION SEED PRODUCERS, INC., Marianna, FL (US)

( * ) Notice: Subject to any disclaimer, the term of this patent is extended or adjusted under 35 U.S.C. 154(b) by 0 days.

(21) Appl. No.: 17/803,051

(22) Filed: Jan. 26, 2022

(65) Prior Publication Data

US 2022/0248585 P1 Aug. 4, 2022

Related U.S. Application Data

(60) Provisional application No. 63/206,153, filed on Jan. 29, 2021.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ... A01H 5/08; A01H 5/00; A01H 5/02; A01H 6/36; A01H 6/368
See application file for complete search history.

(56) References Cited

U.S. PATENT DOCUMENTS

PP10,675 P * 11/1998 Lyrene ..... Plt./157
PP12,165 P2 * 10/2001 Lyrene ..... A01H 6/368 Plt./157
PP19,503 P3 * 11/2008 Lyrene ..... A01H 6/368 Plt./157
PP20,642 P2 * 1/2010 Wright ..... Plt./157
PP20,695 P2 * 2/2010 Wright ..... Plt./157
PP26,917 P3 * 7/2016 Wright ..... A01H 6/368 Plt./157
PP31,007 P3 * 11/2019 Wright ..... A01H 6/368 Plt./157

OTHER PUBLICATIONS

Plant Varieties Journal Quarter Two 2018, vol. 31, NumberTwo, retrieved on Apr. 21, 2022 at https://www.ipaustralia.gov.au/sites/default/files/journals/pvj_31_2_0.pdf, pp. 1 and 55. (Year: 2018).*

* cited by examiner

*Primary Examiner* — June Hwu
(74) *Attorney, Agent, or Firm* — Baker & McKenzie LLP

(57) ABSTRACT

The new blueberry plant variety 'C13-051' is provided. 'C13-051' is a commercial variety intended for the fresh market. The variety is produced from a cross of unpatented parents 'FL09-001' and 'FL05-383'.

5 Drawing Sheets

Latin name of the, genus and species:
Genus—*Vaccinium.*
Species—*corymbosum* hybrid.
Variety denomination: The new blueberry plant claimed is of the variety denominated 'C13-051'.

BACKGROUND OF THE INVENTION

The new variety 'C13-051' was selected from a population of seedlings derived from crossing the blueberry varieties known as 'FL09-001' (unpatented seed parent) and the variety known as 'FL05-383' (unpatented pollen parent). The cross was made in 2009 in Florida, USA and the seed was sown and grown in Corindi Beach, New South Wales, Australia. The new variety was selected in 2013 from among plants located on land at Corindi Beach and assigned the breeding code 'C13-051'. Plants of 'C13-051' were propagated by cuttings for further evaluation and resulted to be uniform and stable. The new variety showed distinctive traits such as evergreen, with fruit of good flavor.

SUMMARY OF THE INVENTION

Asexual reproduction of the new variety 'C13-051' by cutting propagation since 2013 at Corindi Beach, New South Wales, Australia has demonstrated that the new variety reproduces true to type plants.

The new variety was selected in 2013 as a single plant within a population of seedlings resulting from controlled cross of *Vaccinium* varieties. The seedling population was planted in an experimental block in the field at Corindi Beach, New South Wales, Australia and the selection of the new variety took place in the same block. Selection criteria were a combination of early to mid harvest season, similar to that of the comparator variety 'C99-042', low chilling requirement, medium vigour, non-deciduous type of plant (evergreen), large fruit size, good fruit flavor, and firm fruit. The new variety was subsequently evaluated for six years at the commercial farm at Corindi Beach, New South Wales, Australia.

The following characteristics of the new variety have been repeatedly observed and can be used to distinguish 'C13-051' as a new and distinct variety of *Vaccinium corymbosum* hybrid:

1. Non-deciduous (Evergreen).
2. Early to medium season crop
3. High yield
4. Low chilling requirement, estimated to be between 0 and 300 hours
5. Large fruit size, average 3.1 g
6. Excellent fruit flavor The new blueberry variety 'C13-051' has maintained its distinguished characteristics throughout successive asexual propagation. The variety has been repeatedly asexually reproduced through softwood cuttings in New South Wales, Australia and the clones are phenotypically identical to the original plant.

BRIEF DESCRIPTION OF THE DRAWINGS

The accompanying photographic illustration shows typical specimens in full color of the foliage and fruit of the new variety 'C13-051'. The colors are as nearly true as is reasonably possible in a color representation of this type.

Figure 1:
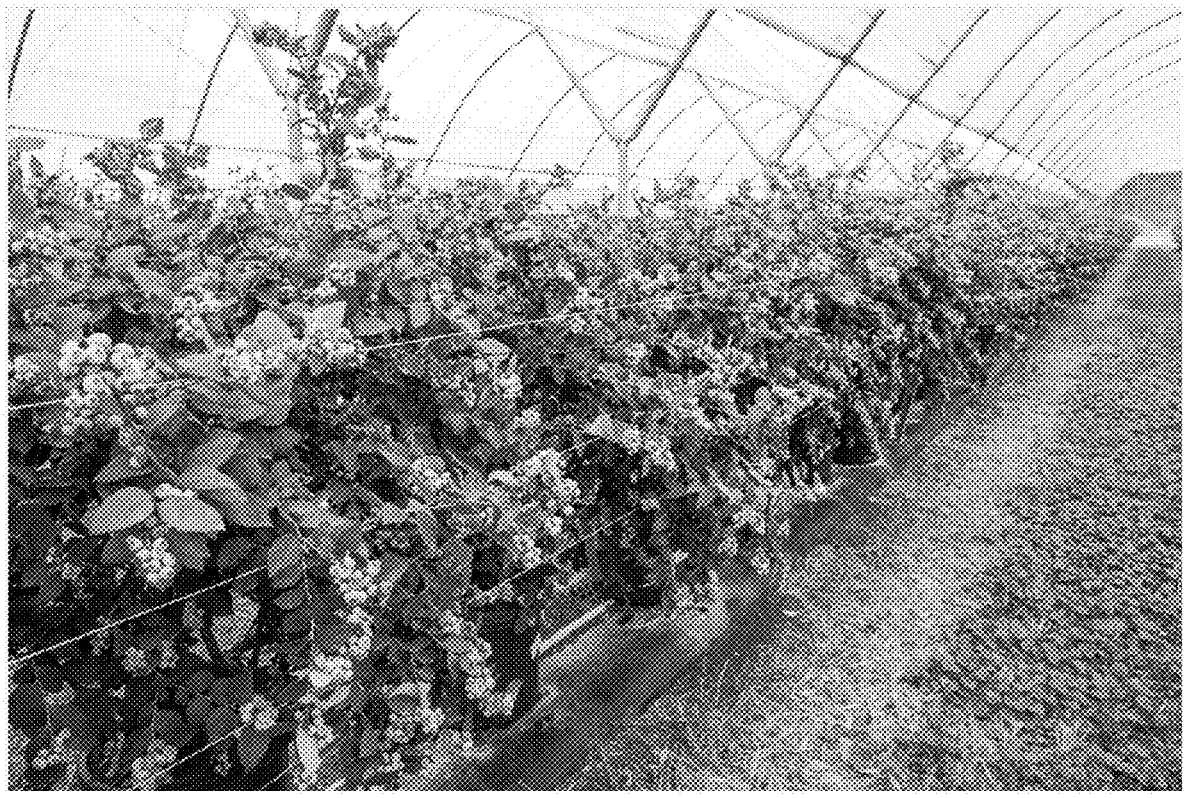
FIG. 1 is a photograph of the new variety 'C13-051', showing 3 year old plants growing in a substrate system.
Figure 2:
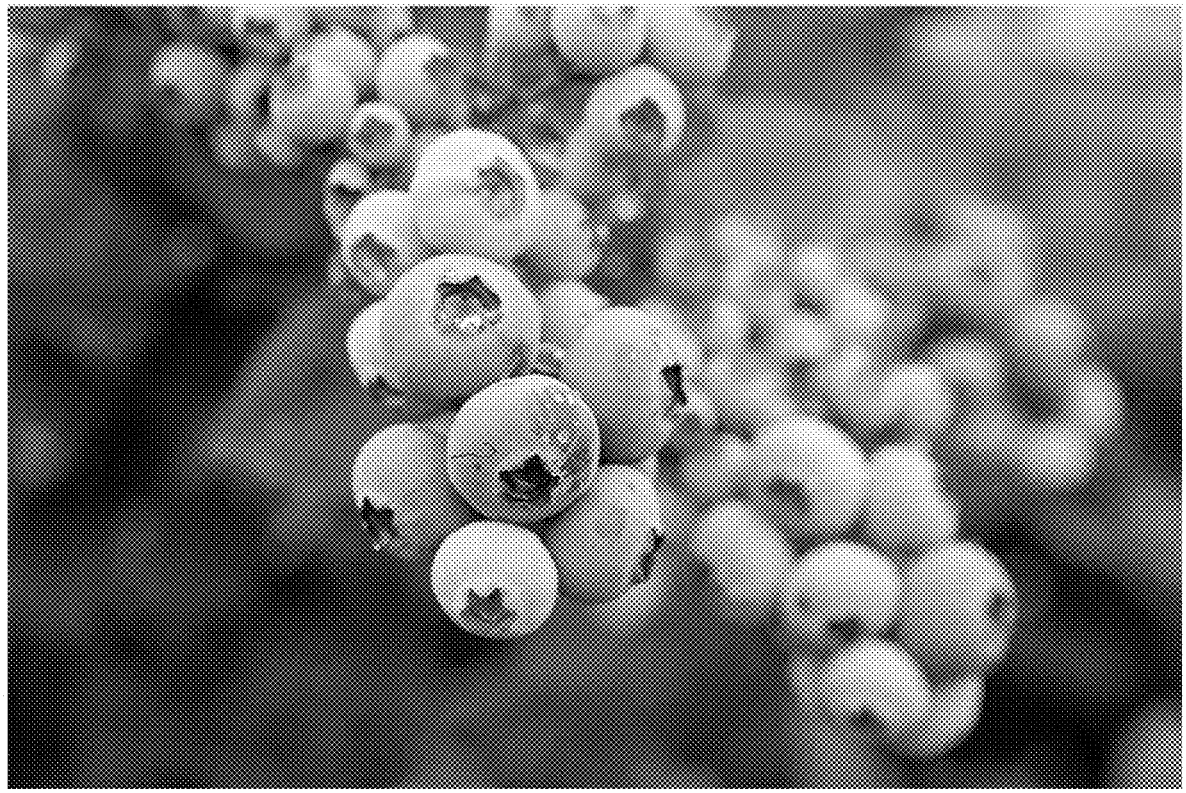
FIG. 2 is a photograph of the new variety 'C13-051', showing a typical dense fruit cluster.
Figure 3:
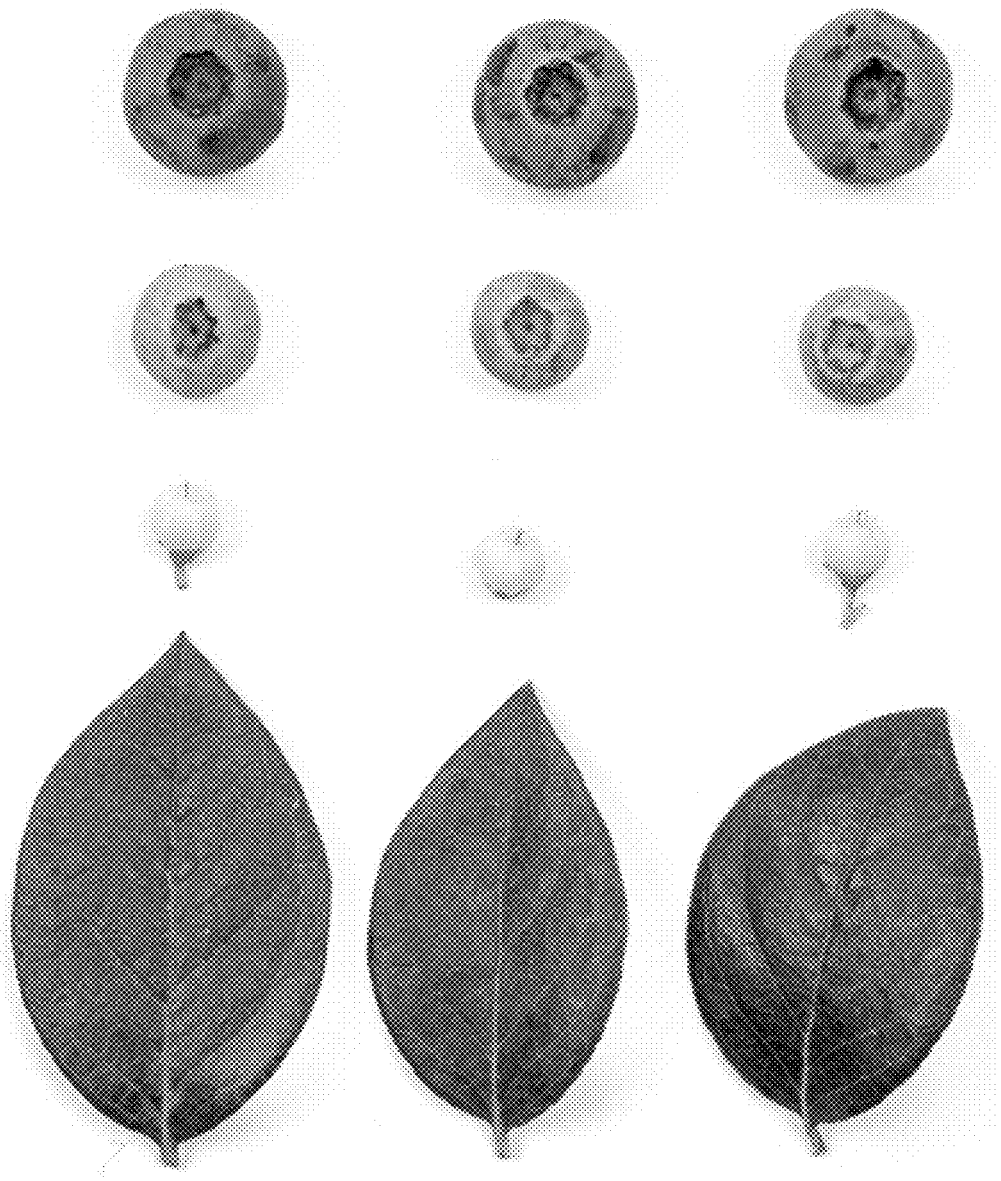
FIG. 3 is a photograph of the new variety 'C13-051' showing the botanical parts of the plants (ripe fruit, green fruit, flowers and leaves).
Figure 4:
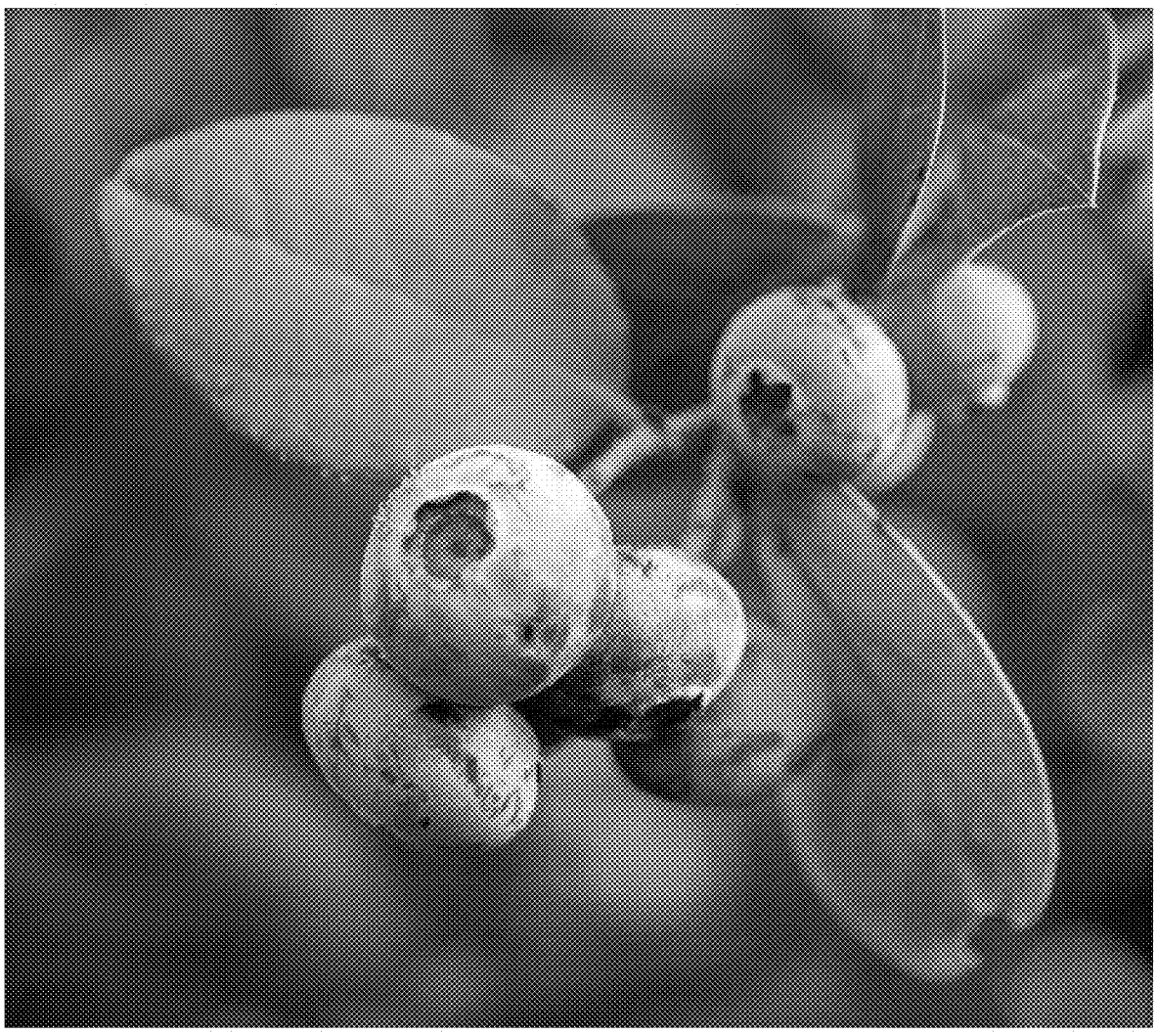
FIG. 4 is a photograph showing the large fruit size of the new variety 'C13-051'. In particular the ripe fruit on the bush.
Figure 5:
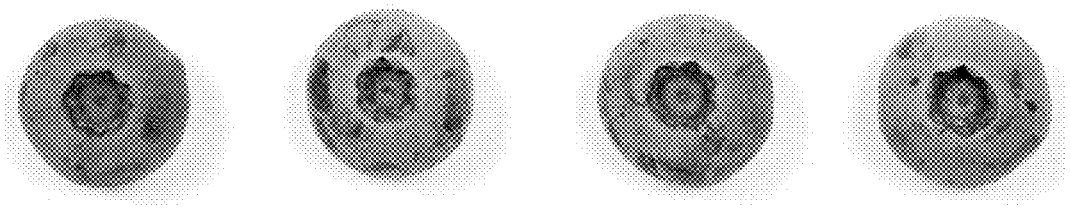
FIG. 5 is a photograph of showing a typical calyx of fruit of 'C13-051'.

The colors in the photographs are as close as possible with the photographic and printing technology utilized. The color values cited in the detailed botanical description accurately describe the colors of the new blueberry variety.

DETAILED BOTANICAL DESCRIPTION

The following detailed description sets forth the distinctive characteristics of 'C13-051'. The data which defines these characteristics was collected from asexual reproductions of the original selection. Dimensions, sizes, colors, and other characteristics are approximations and averages set forth as accurately as possible. For all traits data was collected from 3 plant parts across 6 randomly selected plants. For the traits relating to fruits (e.g., fruit weight, firmness, brix, acidity) the data is an average across twenty fruits collected randomly. The plant history was taken on plants approximately 3 years of age, and the descriptions relate to plants grown in the field in Corindi Beach, New South Wales, 2456 Australia. Descriptions of fruit characteristics were made on fruit grown in Corindi Beach, New South Wales, 2456 Australia. Color designations are from the 2007 edition of The Royal Horticultural Society ("R.H.S.") Colour Chart. 'C12-122' has not been observed under all possible environments. The phenotype may vary slightly with different growing environments such as temperature, light, fertility, soil pH, moisture and maturity levels, but without any change in the genotype.

Classification:

*a. Family.*—Ericaceae.
*b. Genus.*—*Vaccinium.*
*c. Species.*—*corymbosum* hybrid.
*d. Common name.*—Blueberry.

Parentage:

*Female parent.*—Unpatented selection 'FL09-001'.
*Male Parent.*—Unpatented selection 'FL05-383'.

Market class: Fresh market.

PLANT

General:

*Parentage.*—FL09-001 x FL05-383.
*Plant height.*—1.3 m.
*Plant width.*—1.3 m.
*Growth habit.*—Semi-upright.
*Growth.*—Medium vigour.
*Mature cane length.*—0.63 m.
*Mature cane width.*—13.8 mm.
*Mature cane colour.*—Grey-brown group, similar to 199A, and streak of grey-brown 199D.
*Bark texture.*—Medium (texture between rough and smooth).
*Fruiting wood in length.*—31.0 cm.
*One-year-old shoot's color designation.*—Green group, similar to 138A.
*One-year-old shoot's average length of the internode.*—27.4 mm.
*Productivity.*—High yield, 7.5 Kg per plant (estimated equivalent production of 16.5 pounds per plant) from 3-year-old plants when growing in 17 L pots at Corindi Beach, NSW. The plants are spaced at 0.7 m apart along the row and 2.5 m between the rows, which gives an estimated plant density of 5700 plants per hectare.
*Cold hardiness.*—Low chill (USDA plant hardiness Zone 4).
*Cold tolerance.*—Low.
*Chilling requirement.*—Low, estimated between 0 and 300 hours.
*Tolerance to disease.*—None assessed.
*Leafing.*—Overall strong and plant retains leaves during the winter.
*Twigginess.*—Low.

FOLIAGE

General:

*Leaf color (top side).*—Green group, similar to 139A.
*Leaf color (under side).*—Green group, similar to N138C.
*Leaf arrangement.*—Alternate.
*Leaf shape.*—Elliptic.
*Leaf margins.*—Entire.
*Leaf venation.*—Reticulate.
*Leaf length.*—Medium (average 56.2 mm).
*Leaf width.*—Broad (average 34.5 mm).
*Leaf length/width ratio.*—1.6.
*Shape of the leaf apex.*—Acute.
*Shape of the leaf base.*—Cuneate.
*Leaf nectaries.*—Absent.
*Pubescence of upper side.*—Absent.
*Pubescence of lower side.*—Absent.
*Cross sectional profile.*—Flat.
*Longitudinal profile.*—Straight.
*Attitude.*—Horizontal.

Petioles:
*Length*.—Average 3.5 mm.
*Width*.—Average 1.48 mm.
*Color*.—Yellow green 144D.

FLOWERS

General:
*Time of beginning of flowering*.—Early to mid-season (50% of anthesis estimated to be on the third week in June, on 3 year old plants, cultivated at Corindi Beach, NSW).
*Flower shape*.—Urceolate.
*Flower fragrance*.—None perceptible.
Corolla:
*Shape*.—Urceolate.
*Color*.—White group, similar to NN155C.
*Length*.—7.1 mm.
*Width*.—7.9 mm.
*Aperture width*.—3.09 mm.
*Anthocyanin coloration of corolla*.—Absent or very weak.
*Corolla ridges*.—Present, average of 5.
*Protrusion of stigma*.—Present.
*Corolla/petal texture*.—Smooth.
Inflorescence:
*Inflorescence length*.—Average 21.35 mm.
*Inflorescence width*.—19.9 mm.
*Length of peduncle*.—19.98 mm.
*Surface texture of peduncle*.—Medium (texture between rough and smooth).
*Color of peduncle*.—Base color is yellow-green group 145C, over color is greyed-red group 182A.
*Length of pedicel*.—8.45 mm.
*Surface texture of pedicel*.—Smooth.
*Color of pedicel*.—Yellow green group 145A and 145C.
*Number of flowers per cluster*.—11.
*Flower cluster density*.—Dense.
*Flowering interval on one-year old shoot*.—July to August.
*Flowering interval on current year shoot*.—July to August.
Calyx (with sepals):
*Diameter*.—4.8 mm.
*Color of sepal's outside*.—Green group, similar to 144A.
*Color of sepal's inside*.—Green group, similar to 144C.
Stamen:
*Length*.—6.06 mm.
*Number per flower*.—10.
*Filament color*.—Similar to yellow-green group 145C.
Pistil:
*Pistil length* (*including ovary*).—10.08 mm.
*Style length* (*including stigma*).—8.14 mm.
*Style color*.—Similar to yellow-green group N144B and 145B.
Anther:
*Length*.—3.65 mm.
*Number*.—10.
*Color*.—Similar to greyed-orange group 165A.
Pollen:
*Abundance*.—Abundant.
*Color*.—Yellow group, similar to 10C.
*Self-compatibility*.—Yes, this variety shows a high degree of self compatibility.

FRUIT

General:
*Time of fruit ripening*.—Early to mid-season, estimated 50% of the fruit ripe on the 1st September, on 3-year-old plants, growing at Corindi Beach, NSW.
*Plant fruiting type*.—One-year-old and current seasons shoots.
*Cluster density*.—Dense (8-11 berries per cluster).
*Unripe fruit color*.—Similar to yellow-green group 144A.
*Ripe berry color*.—Blue group 103A, when bloom is removed.
*Berry surface wax abundance*.—Weak to medium.
*Berry weight*.—On average 3.1 g.
*Berry height from calyx to scar*.—13.3 mm.
*Berry diameter*.—18.5 mm.
*Berry shape*.—Oblate.
*Fruit diameter of calyx basin*.—Small, on average 4.6 mm.
*Fruit depth of calyx basin*.—Medium.
*Fruit stem scar*.—Large.
*Sweetness when ripe*.—High (14 Brix).
*Firmness when ripe*.—Firm, 180 g/mm, measured with FirmTech.
*Acidity when ripe*.—Medium (0.5%).
*Berry flesh color*.—Yellow-green group, similar to 145C.
*Storage quality*.—Low shelf life, an average of 16 days.
*Suitability for mechanical harvesting*.—Not tested.
*Uses*.—Fruit to be hand harvested for fresh market.

SEED

General:
*Seed abundance in fruit*.—Abundant, on average 29 seeds per fruit.
*Seed color*.—Greyed orange group 166B.
*Seed length*.—1.8 mm.

COMPARISON WITH SIMILAR CULTIVARS

Table 1 below provides a comparison between C13-051 and similar cultivars:

TABLE 1

Comparison of 'C13-051' with similar cultivars

| Characteristics | 'C13-051' | 'C99-42' (U.S. Plant Pat. No. 20,695P2) | 'Snowchaser' (U.S. Plant Pat. No. 19,503P3) |
|---|---|---|---|
| Plant vigour | Medium | Weak to medium | Medium |
| Plant growth habit | Semi-upright | Semi-upright to intermediate | Semi-upright |
| One year old shoot length of internodes | Medium | Very short to short | Short |
| Leaf length | Medium | short | Long |
| Leaf length (mm) | 56.2 ± 2.3 | 53.10 ± 0.8 | 61.50 ± 0.9 |
| Leaf width | Broad | Very narrow to narrow | Broad |

TABLE 1-continued

Comparison of 'C13-051' with similar cultivars

| Characteristics | 'C13-051' | 'C99-42' (U.S. Plant Pat. No. 20,695P2) | 'Snowchaser' (U.S. Plant Pat. No. 19,503P3) |
|---|---|---|---|
| Leaf width (mm) | 34.5 ± 2 | 22.9 ± 1.3 | 34.3 ± 1.5 |
| Flower size of corolla | Small | medium | Medium |
| Flower corolla length (mm) | 7.1 ± 0.2 | 9.7 ± 0.3 | 9.5 ± 0.3 |
| Fruit cluster density | Dense | sparse | Medium |
| Fruit size | Large | Small to medium | Small to medium |
| Fruit weight (g) | 3.1 ± 0.43 | 1.9 ± 0.39 | 1.7 ± 0.21 |
| Fruit diameter (mm) | 18.5 ± 0.66 | 15.6 ± 0.96 | 15.10 ± 0.97 |
| Fruit depth of calyx basin | Medium | Medium | Shallow |
| Fruit intensity of bloom | Weak to medium | Weak to medium | Weak to medium |
| Fruit firmness | Firm | Firm | soft |
| Soluble solid content (%) | 14 | 13.1 | 14 |

TABLE 1-continued

Comparison of 'C13-051' with similar cultivars

| Characteristics | 'C13-051' | 'C99-42' (U.S. Plant Pat. No. 20,695P2) | 'Snowchaser' (U.S. Plant Pat. No. 19,503P3) |
|---|---|---|---|
| Titratable acidity (%) | 0.5 | 0.4 | 0.7 |
| Time of vegetative bud burst | Medium | early | early |
| Time of beginning of flowering | Early to medium | Early to medium | Very early to early |
| Time of beginning of fruit ripening | Early to medium | Early to medium | Very early to early |

The invention claimed is:

1. A new and distinct variety of blueberry plant named 'C13-051', substantially as illustrated and described herein.

* * * * *